(12) United States Patent
Suzuki

(10) Patent No.: US 10,316,427 B2
(45) Date of Patent: Jun. 11, 2019

(54) METHOD FOR THE PRODUCTION OF SINGLE CRYSTALLINE MGTIO3 FLAKES

(71) Applicant: Merck Patent GmbH, Darmstadt (DE)

(72) Inventor: Ryuta Suzuki, Fukushima-ken (JP)

(73) Assignee: Merck Patent GmbH, Darmstadt (DE)

( * ) Notice: Subject to any disclaimer, the term of this patent is extended or adjusted under 35 U.S.C. 154(b) by 72 days.

(21) Appl. No.: 15/104,690

(22) PCT Filed: Nov. 20, 2014

(86) PCT No.: PCT/EP2014/003099
§ 371 (c)(1),
(2) Date: Jun. 15, 2016

(87) PCT Pub. No.: WO2015/090500
PCT Pub. Date: Jun. 25, 2015

(65) Prior Publication Data
US 2016/0312378 A1    Oct. 27, 2016

(30) Foreign Application Priority Data

Dec. 20, 2013 (EP) .................................... 13005968

(51) Int. Cl.
*C30B 1/00* (2006.01)
*C30B 1/02* (2006.01)
(Continued)

(52) U.S. Cl.
CPC .............. *C30B 1/02* (2013.01); *A61K 8/0254* (2013.01); *A61K 8/29* (2013.01); *A61Q 1/02* (2013.01); *A61Q 17/04* (2013.01); *B01J 21/10* (2013.01); *B01J 35/004* (2013.01); *C08K 3/22* (2013.01); *C09C 1/36* (2013.01); *C09D 7/61* (2018.01); *C30B 1/10* (2013.01); *C30B 7/04* (2013.01); *C30B 9/12* (2013.01); *C30B 29/32* (2013.01); *C30B 29/60* (2013.01); *A61K 2800/412* (2013.01); *C08K 2003/2237* (2013.01); *H01G 9/2027* (2013.01)

(58) Field of Classification Search
CPC ............ C30B 29/32; C08K 2003/2217; C08K 2003/2237; C09C 1/36; A61K 8/0254
USPC .................................... 423/598, 71; 428/402
See application file for complete search history.

(56) References Cited

U.S. PATENT DOCUMENTS

2002/0197461 A1* 12/2002 Takaya ................... B32B 18/00
428/210

FOREIGN PATENT DOCUMENTS

EP        1148030 A1    10/2001
EP        1415955 A1    5/2004
(Continued)

OTHER PUBLICATIONS

International Search Report dated Jul. 15, 2016, issued in corresponding PCT/EP2014/075850, 3 pages.
(Continued)

*Primary Examiner* — Steven J Bos
(74) *Attorney, Agent, or Firm* — Millen White Zelano and Branigan, PC; Csaba Henter

(57) ABSTRACT

The present invention is related to a method for the production of single crystalline $MgTiO_3$ flakes, in particular in the geikielite crystal structure, to single crystalline $MgTiO_3$ flakes obtained by this method as well as to the use thereof, in particular as pigments in several application media.

20 Claims, 1 Drawing Sheet

(51) Int. Cl.

| | | |
|---|---|---|
| *A61K 8/29* | (2006.01) | |
| *A61Q 1/02* | (2006.01) | |
| *A61Q 17/04* | (2006.01) | |
| *A61K 8/02* | (2006.01) | |
| *C30B 7/04* | (2006.01) | |
| *C30B 9/12* | (2006.01) | |
| *C30B 29/32* | (2006.01) | |
| *C30B 29/60* | (2006.01) | |
| *B01J 21/10* | (2006.01) | |
| *B01J 35/00* | (2006.01) | |
| *C08K 3/22* | (2006.01) | |
| *C09C 1/36* | (2006.01) | |
| *C30B 1/10* | (2006.01) | |
| *C09D 7/61* | (2018.01) | |
| *H01G 9/20* | (2006.01) | |

(56) References Cited

FOREIGN PATENT DOCUMENTS

| FR | 2936513 A | 4/2010 |
|---|---|---|
| JP | H05-136117 A | 6/1993 |
| JP | 2004-010464 A | 1/2004 |
| JP | 2010-002367 A | 1/2010 |
| WO | 2010/038205 A1 | 4/2010 |

OTHER PUBLICATIONS

Haider, A.F.M.Y. et al., "ESR study of transition metal ions in magnesium titanate", XP020005100, Journal of Physics C, vol. 13, No. 33. 190, pp. 6239-6250.

Hautefeuille, P., "Etudes sur la repreoduction des mineraux titanif GBP eres", XP008174146, Annales de Chimie et de Physique, vol. 4, 1865, pp. 129-176.

Stubicar, N. et al., "Microstructural evolution of some MgO-TiO2 and MgO-Al2O3 powder mixtures during high-energy ball milling and post-annealing studied by X-ray diffraction", X9004502537, Journal of Alloys and Compounds, vol. 370, No. 1-2, 2004, pp. 296-301.

Tobin, L. et al., "Characterising dye-sensitised solar cells", XP028215435, Optik, vol. 122, No. 14, 2010, p. 1225-1230.

English translation Abstract of JPH05-136117A published Jun. 29, 1993 (1 page).

English translation Abstract of JP2010-002367A published Jan. 7, 2010 (1 page).

Office Action in corresponding JP application JP2016541563A dated May 31, 2018.

* cited by examiner

METHOD FOR THE PRODUCTION OF SINGLE CRYSTALLINE MGTIO3 FLAKES

BACKGROUND OF THE INVENTION

1. Field of the Invention

The present invention relates to a method for the production of single crystalline $MgTiO_3$ flakes, to single crystalline $MgTiO_3$ flakes produced by this method as well as to the use thereof, in particular as pigments.

2. Description of the Related Art

Inorganic pigments such as mica, talc, glass flakes, MIO (micaceous iron oxide) and so on have been used for a long time in formulations such as paints, films, coating compositions and cosmetics for several purposes, either coated or uncoated.

In addition to the usually used inorganic particles as mentioned above, titanate particles have been proven to be useful for several purposes in coatings and compositions. Titanates exhibit electrical properties such as piezoelectricity and conductivity, mechanical properties such as abrasion-extinguishing and reinforcing, as well as chemical properties such as hydrophilicity and surface activity. By now, titanates are used in various applications such as ceramic capacitors, photocatalysts, semiconductors and electrode materials. As the titanates, potassium titanate, barium titanate, strontium titanate, calcium titanate, magnesium titanate, lead titanate, aluminum titanate and lithium titanate are of particular interest.

Titanate powders which are composed of flaky titanate particles are in their dispersibility and orientation behavior comparable to classic inorganic pigments like mica or talc which exhibit a naturally excellent dispersibility and orientation based on the flaky shape thereof. Therefore, titanate flakes are desired which might be used as pigments and bulking agents.

For example, Japanese Unexamined Patent Application Publication No. 05-163117 (Patent Document 1) discloses flakes of polycrystalline potassium hexatitanate ($K_2Ti_6O_{13}$) which either contain color imparting metal ions or are coated with a metal oxide and are used as extender pigment or coloring pigment. The process for the production of the polycrystalline flakes needs at least two heating steps with temperatures above about 500° C.

Japanese Unexamined Patent Application Publication No. 2008-162971 (Patent Document 2) discloses platy titanate crystal particles ($K_{3-x}Li_xTi_{2-x}O_4$, $K_{2-x}Mg_xTi_{2-x}O_4$, or $K_xFe_xTi_{2-x}O_4$, with $0.05 \leq x \leq 0.5$ in every case) of the lepidocrocite type which exhibit a particular size range and are produced by a flux growth process, as well as their use as bright pigment and bulking agent. Here too, the process for the production of the platy titanate particles includes at least two heating steps with temperatures of $\geq 800°$ C.

The production methods described in these Patent Documents need to be improved further from the view point of efficiency.

For example, potassium hexatitanate ($K_2Ti_6O_{13}$) flakes obtained by the method described in Patent Document 1 are polycrystalline. Therefore, their refractive index is lower than for a single crystalline titanate of the same composition. Furthermore, the requirement of one high temperature heat melting step and one high temperature calcination step takes time, is costly and causes more complications in the production process.

Similar thereto, the production process for the lepidocrocite type platy titanate crystal particles obtained by the method described in Patent Document 2 does also require two high temperature calcination steps which take time, are costly and cause more complications in the producing step.

The present inventors focused on magnesium titanate which has good dielectric properties, biocompatibility and exhibits anisotropic thermal expansion, and developed a process for the production of magnesium titanate particles which might be used in several usual pigment applications.

The aim of the present invention is to offer a production method having reduced energy cost and, thus, offering a method to effectively produce single crystalline $MgTiO_3$ flakes suitable for use as pigments in various applications, to offer magnesium titanate single crystalline flakes produced by this method as well as to show how they may be used.

SUMMARY OF THE INVENTION

The inventors have found that the problems described above can be solved and that single crystalline $MgTiO_3$ flakes suitable for use as pigments can be effectively produced by mixing a phosphorus compound with a titanium compound in the presence of a magnesium compound in order to form a $MgTiO_3$ precursor and then by calcination the obtained precursor, and completed the present invention.

The present invention is following.

(1) A method for the production of single crystalline $MgTiO_3$ flakes by the following steps:
1. mixing at least a titanium compound, a magnesium compound and a phosphorous compound whereby a $MgTiO_3$ precursor is formed; and
2. calcining the $MgTiO_3$ precursor at a temperature in the range from 800° C. to 1400° C. as a single calcination step.

(2) The method according to (1), wherein the mixing is executed in an aqueous medium.

(3) The method according to any one of (1) or (2), wherein a fluxing agent is present in the mixing step.

(4) The method according to (3), wherein the fluxing agent is a compound selected from one or more of $Na_2SO_4$, $K_2SO_4$, NaCl and KCl.

(5) The method according to any one of (2) to (4), wherein the method comprises drying of the $MgTiO_3$ precursor prior to the calcination step.

(6) The method according to any one of (1) to (5), wherein the calcining is executed in an oxygen containing atmosphere.

(7) The method according to any one of (3) to (6), wherein a product obtained in the calcination step according to (3) is treated with hot water.

(8) The method according to any one of (1) to (7), wherein the titanium compound is a compound selected from one or more of titanium tetrachloride, titanyl sulfate, titanium sulfate and titanium trichloride.

(9) The method according to any one of (1) to (8), wherein the magnesium compound is a compound selected from one or more of magnesium chloride, magnesium sulfate and magnesium carbonate.

(10) The method according to any one of (1) to (9), wherein the phosphorous compound is a compound selected from one or more of trisodium phosphate, phosphorous pentoxide, phosphoric acid, phosphorous acid and tripotassium phosphate.

(11) Single crystalline $MgTiO_3$ flakes obtained by the method according to any one of (1) to (10).

(12) Single crystalline $MgTiO_3$ flakes according to (11), having a geikielite crystal structure.

(13) Single crystalline $MgTiO_3$ flakes according to (11) or (12), having a particle diameter in the range of 10 to 100 µm, according to an equivalent of the corresponding circle diameter.

(14) Use of single crystalline $MgTiO_3$ flakes according to any one of (11) to (13) in a paint, ink, coating composition, plastic or cosmetic.

(15) Use according to (14) as white pigment, photo catalyst, host material for dye sensitized solar cells, UV absorbent or water repellent.

According to the present invention, a method to effectively produce single crystalline $MgTiO_3$ flakes which are suitable for use as pigments can be offered.

BEST MODE FOR CARRYING OUT THE INVENTION

Hereinafter, the method for the production of single crystalline $MgTiO_3$ flakes according to the present invention and the single crystalline $MgTiO_3$ flakes obtained by this method will be described in detail. However, the present invention is not limited to these particular embodiments as long as the intention of the present invention is followed.

The method for the production of single crystalline $MgTiO_3$ flakes according to a first embodiment of the present invention (hereinafter, abbreviated to "the production method of the present invention") contains: "a step of mixing at least a titanium compound, a magnesium compound and a phosphorous compound whereby a $MgTiO_3$ precursor is formed"; and "a step of calcining the $MgTiO_3$ precursor at a temperature in the range from 800° C. to 1400° C. as a single calcination step".

The inventors have found that single crystalline $MgTiO_3$ flakes suitable for use as pigments can be effectively produced by mixing a phosphorus compound with a titanium compound and a magnesium compound in order to form a $MgTiO_3$ precursor, and then by calcination of the obtained precursor in a single calcination step. The single crystalline $MgTiO_3$ flakes have a high refractive index and high luster, therefore, they are particularly suitable as highly reflective pigments, especially interference pigments, or as substrates for interference pigments. The production method of the present invention enables an effective production of good quality single crystalline $MgTiO_3$ flakes with the need for only one single calcination step. Therefore, this method is highly suitable for the suppression of producing cost and efforts. Furthermore, it can produce single crystalline $MgTiO_3$ flakes, in which twin crystals and coagulations hardly occur and in which crystallinity is high and diameter control is possible. Therefore, single crystalline $MgTiO_3$ flakes in the geikielite crystal structure having a high refractive index can be produced.

Although the detailed mechanisms for the formation of single crystalline $MgTiO_3$ flakes according to the present invention have not been sufficiently clarified, the inventors have confirmed that $MgTiO_3$ flakes have been formed with a titanium compound and a magnesium compound under the co-existence of phosphorus ions.

Hereinafter, the production method of the present invention will be described in detail.

The production method of the present invention contains as the first step a step of mixing at least a titanium compound, a magnesium compound and a phosphorous compound whereby a $MgTiO_3$ precursor is formed (hereinafter, abbreviated to "mixing step").

In the first and most simple embodiment of the present invention, the concrete types for the titanium compound, the magnesium compound and for the phosphorus compound as well as a concrete method for mixing are not limited to any specifics as long as the $MgTiO_3$ precursor can be formed. Since the formation of a $MgTiO_3$ precursor will occur even if pure titanium is used, the $MgTiO_3$ precursor is formed independently of the kind of starting materials for the titanium compound, the magnesium compound and the phosphorous compound, respectively. Here, the "$MgTiO_3$ precursor" is considered to contain titanium oxide hydrate and magnesium oxide hydrate as the mayor components.

As a second step, the production method according to the present invention contains a step of calcining the $MgTiO_3$ precursor at a temperature in the range from 800° C. to 1400° C. as a single calcination step (hereinafter, abbreviated to "calcination step").

The calcination temperature in the present production method is usually at least 800° C., and more preferably at least 900° C. Also it is usually at most 1400° C. and more preferably at most 1250° C. from the view point of producing a crystalline substance. Thus, the most preferred temperature range for the single calcination step is of from 900° C. to 1250° C.

The calcination time should be appropriately selected according to the desired shape of the single crystalline $MgTiO_3$ flakes (particle diameter, thickness, and aspect ratio). It is usually at least 5 minutes, preferably at least 10 minutes, and more preferably at least 2 hours. Further, this value is usually at most 12 hours, preferably at most 10 hours, and more preferably at most 5 hours.

The calcination atmosphere is not limited to any specifics as long as $MgTiO_3$ can be formed. However, in order to reliably produce the oxide, the calcination step is preferably carried out under oxygen containing atmosphere.

The concrete method for mixing of the titanium compound, the magnesium compound and the phosphorus compound at the mixing step is not limited to any specifics, however, they are preferably mixed in an aqueous medium because working in aqueous solution is comfortable and easy to handle. If the mixing step according to the present invention is executed in an aqueous medium, this variation of the present process represents the second embodiment of the present invention.

The addition of the magnesium compound to the aqueous medium may be carried out prior to the addition of the titanium compound, at the same time as the addition of the titanium compound, or after the addition of the titanium compound. However, when the magnesium compound is added to the aqueous medium prior to the addition of the titanium compound, the yield of the $MgTiO_3$ flakes may be increased. Therefore, the latter sequence is preferred.

The addition of the phosphorus compound to the aqueous medium may be carried out prior to the addition of the titanium compound, at the same time as the addition of the titanium compound, or after the addition of the titanium compound. However, when the phosphorus compound is added to the aqueous medium prior to the addition of the titanium compound, the yield of the $MgTiO_3$ flakes may be increased. Therefore, the latter sequence is preferred.

When the mixing is carried out within an aqueous medium, it is preferred to hold the aqueous solution at a pH value in the region of from 6 to 8 in order to avoid damage to the crucible by gas generated during calcining. For example, when an acidic titanium compound such as titanium tetrachloride is added to the aqueous solution containing a basic phosphorus compound such as trisodium phosphate, this solution is neutralized fully or at least to a certain degree.

Further, the pH value may be adjusted to 6 to 8 by separately adding an acidic solution such as hydrochloric acid or sulfuric acid or basic solution such as sodium hydroxide aqueous solution or sodium carbonate.

Furthermore, it is desirable for the addition of the titanium compound to be carried out gradually over a longer time period in order to suppress a rapid pH variation.

According to the present invention, the "aqueous medium" indicates the medium mainly comprising tap water or purified water and may also be an aqueous solution comprising another component in addition to the pure water such as deionized water.

According to a third embodiment of the present invention, it is preferred that a fluxing agent is added to the above mentioned starting materials prior to the calcination step. Here, the "fluxing agent" indicates a type of compound, in particular a metal salt, that functions as a dissolution means in a so called "fluxing growth process", which leads to the formation of $MgTiO_3$ from the $MgTiO_3$ precursor at the calcination step.

For being useful as a fluxing agent in the production process according to the present invention, the corresponding metal salts should exhibit a melting temperature which is not less than 800° C. but does not achieve or exceed the melting temperature of the resulting $MgTiO_3$. In addition, they have to be water soluble. Examples are metal salts such as $Na_2SO_4$, $K_2SO_4$, NaCl, and KCl, either alone or in combination of two or more thereof, whereby KCl may only be used in combination with at least one of the other salts mentioned. From the view point of cost and ready availability, $Na_2SO_4$ and $K_2SO_4$ are preferred, and $Na_2SO_4$ is particularly preferred.

Since the addition of a fluxing agent influences the crystal growth process of the resulting pigments, the usage amount of the fluxing agent should be appropriately selected according to the desired shape of the single crystal $MgTiO_3$ flakes (particle diameter, thickness, and aspect ratio). The ratio of the fluxing agent mol number against the Ti atom mol number in the used titanium compound (fluxing agent mol number/Ti atom mol number in the titanium compound), it is usually at least 1.0, and more preferably at least 3.0. Further, this value is usually at most 30, and more preferably at most 10. In case of a ratio of less than 1.0, the salt treatment effect would be insufficient. On the other hand, if the ratio would exceed the value of 30, no further improvement in the flake formation would occur and a larger scale washing step to eliminate them later would be necessary.

The addition of the fluxing agent into the mixture of the starting materials may be executed prior to the addition of the titanium compound, at the same time as the addition of the titanium compound, or after the addition of the titanium compound. However, when the fluxing agent is added after the addition of the titanium compound, the yield of the $MgTiO_3$ flakes may be increased. Therefore, the latter sequence is particularly preferred.

The production method according to the present invention may preferably also contain other steps, in addition to the mixing step and the calcination step. This belongs to the following steps:

drying step of the $MgTiO_3$ precursor, in order to obtain a powder of the molten salt mixture prior to the calcination step (hereinafter, abbreviated to "drying step 1");
The temperature in drying step 1 is preferably in the range of from 70° C. to 180° C., although the method is not limited to this.

in order to remove impurities such as chloride, sulfate, etc, from the product obtained in the calcination step, a step to treat the product obtained at the calcination step with warm water (hereinafter, abbreviated to "washing step"); Warm water used at the washing step is not limited to any specifics, however, purified water and deionized water are preferred. Here, the temperature of the water is preferably in the range of from 40° C. to 100° C. In case a fluxing agent is used for the present production method, such a washing step is indispensable.

in order to separate the $MgTiO_3$ flakes from the solution containing dissolved impurities after the washing step, a step to filter and separate the undissolved solids (the $MgTiO_3$ flakes) after the washing step (hereinafter, abbreviated to "filtration step"); and in order to dry the $MgTiO_3$ flakes, a step to dry the $MgTiO_3$ flakes (hereinafter, abbreviated to "drying step 2"). This drying step is executed preferably in a temperature range of from 20° C. to 180° C., although the present process is not limited thereto.

Regarding the titanium compound which may be used as a starting material for the present production method, water soluble titanium compounds are preferred, in particular in case the process is executed in an aqueous medium. Organic titanium compounds as well as inorganic titanium compounds may be used, but inorganic titanium compounds are clearly preferred. Using water soluble inorganic titanium compounds makes the production process simple and easy to handle, in combination with no need for expensive apparatuses and explosion protection. Inorganic titanium compounds are preferably inorganic titanium salts. Examples of titanium salts are: titanium tetrachloride, titanium oxy sulfate, titanium sulfate and titanium tri-chloride. However, from the view point of cost and ready availability, titanium tetra-chloride and titanium sulfate are preferred. Here, the types of the used titanium compound is not limited to one type and at least two types may be used together.

The usage amount of the titanium compound should be appropriately selected according to the desired amount of the single crystalline $MgTiO_3$ flakes to be produced. As the ratio of Ti atom mol number in the single crystalline $MgTiO_3$ flakes against the mol number in the used titanium compound (Ti atom mol number in single crystalline $MgTiO_3$ flakes/Ti atom mol number of the titanium compound), it is usually at least 0.3, preferably at least 0.4 and more preferably at least 0.5. Further, this value is usually at most 0.9, preferably at most 0.95 and more preferably at most 1.0.

As the magnesium compound, water soluble magnesium compounds are preferred as well, in particular inorganic magnesium salts. Examples of useful magnesium salts are: magnesium chloride, magnesium sulfate and magnesium carbonate. However, from the view point of cost and ready availability, magnesium chloride is preferred. Here, the types of the used magnesium compound is not limited to one type and at least two types may be used together.

The usage amount of the magnesium compound should be appropriately selected according to the desired amount of the single crystalline $MgTiO_3$ flakes to be produced. As the ratio of Mg atom mol number in the single crystalline $MgTiO_3$ flakes against the Mg atom mol number of the used magnesium compound (Mg atom mol number in the single crystalline $MgTiO_3$ flakes/Mg atom mol number in the magnesium compound), it is usually at least 0.3, preferably at least 0.4, and more preferably at least 0.5. Further, this value is usually at most 0.9, preferably at most 0.95 and more preferably at most 1.0.

As the phosphorus compound, phosphate compounds such as phosphoric acid, phosphates, condensed phosphoric acid, and condensed phosphate may be listed, and any one can be used as long as it is water soluble. Among them, from the view point of cost and ready availability, trisodium phosphate, phosphorus pentoxide, phosphoric acid, phosphorrous acid and tri-potassium phosphate are preferred. Trisodium phosphate is particularly preferred. Here, the types of the used phosphorus compound is not limited to one type and at least two types may be used together.

The usage amount of the phosphorus compound should be appropriately selected according to the desired shape of the single crystalline $MgTiO_3$ flakes (particle diameter, thickness, and aspect ratio). As the ratio of phosphorus compound mol number against the Ti atom mol number in the used titanium compound (phosphorus compound mol number/Ti atom mol number in the titanium compound), it is usually at least 0.01, preferably at least 0.1, and more preferably at least 1.0. Further, this value is usually at most 10, preferably at most 7.0, and more preferably at most 5.0.

According to the present production process, high quality single crystalline $MgTiO_3$ flakes may be effectively produced. Thus, a further object of the present invention is single crystalline $MgTiO_3$ flakes produced by the process mentioned above.

The single crystalline $MgTiO_3$ flakes of the present invention will be described in detail now. They usually exhibit the shapes, sizes and crystal structure as described below, although these characteristics are not limited to the values disclosed.

The average particle diameter of the single crystalline $MgTiO_3$ flakes is usually at least 10 μm, preferably at least 20 μm. And this value is usually at most 100 μm, preferably at most 90 μm.

As soon as the average particle diameter of the $MgTiO_3$ flakes is within the region mentioned above, it is possible to obtain a pigment having high luster. Here, the "average particle diameter" expresses a diameter of a circle corresponding to the largest length or width of the flake, and indicates the average value obtained from the particle size distribution based on the volume.

The thickness of the flakes is usually at least 0.1 μm, preferably at least 0.2 μm. And this value is usually at most 0.5 μm, preferably at most 0.4 μm. As long as the thickness is within this region, pearl luster of the resulting $MgTiO_3$ flakes may occur, optionally in combination with interference colour, depending on the actual thickness of the flakes.

The aspect ratio of the flakes is usually at least 20, preferably at least 40. And this value is usually at most 200, preferably at most 100. A high aspect ratio leads to good orientation and, thus, high luster, of the resulting $MgTiO_3$ flakes in any coating layer to which they might be added.

The crystal structure of the $MgTiO_3$ flakes according to the present invention is monocrystalline and of the geikielite type. This crystal structure demonstrates the formation of a genuine mixed oxide rather than of a Mg doped titanium oxide, according to the production process of the present invention.

By means of the production method according to the present invention, single crystalline $MgTiO_3$ flakes which are suitable as pigments, either coated or uncoated, in particular for paints, inks, coating compositions, plastics or cosmetics can be produced. Thus, the use of the present single crystalline $MgTiO_3$ flakes as pigments in paints, inks, coating compositions, plastics or cosmetics is also one object of the present invention. Further, as the single crystalline $MgTiO_3$ flakes of the present invention exhibit a high refractive index, good luster, good dielectric properties as well as anisotropic thermal expansion, they may also be used in photocatalysts, host material for dye sensitized solar cells, UV absorbents and water repellents, to name only a few.

Figure 1:
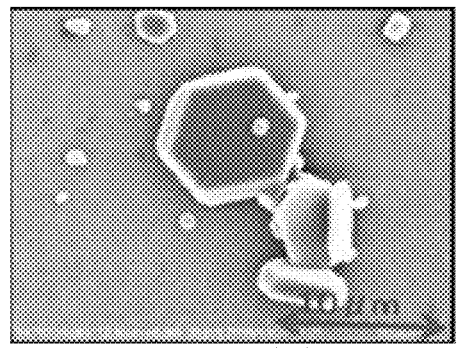
FIG. 1 is a SEM image of the surface of the single crystalline $MgTiO_3$ flakes obtained by the production method in accordance with an embodiment of the present invention.
Figure 2:
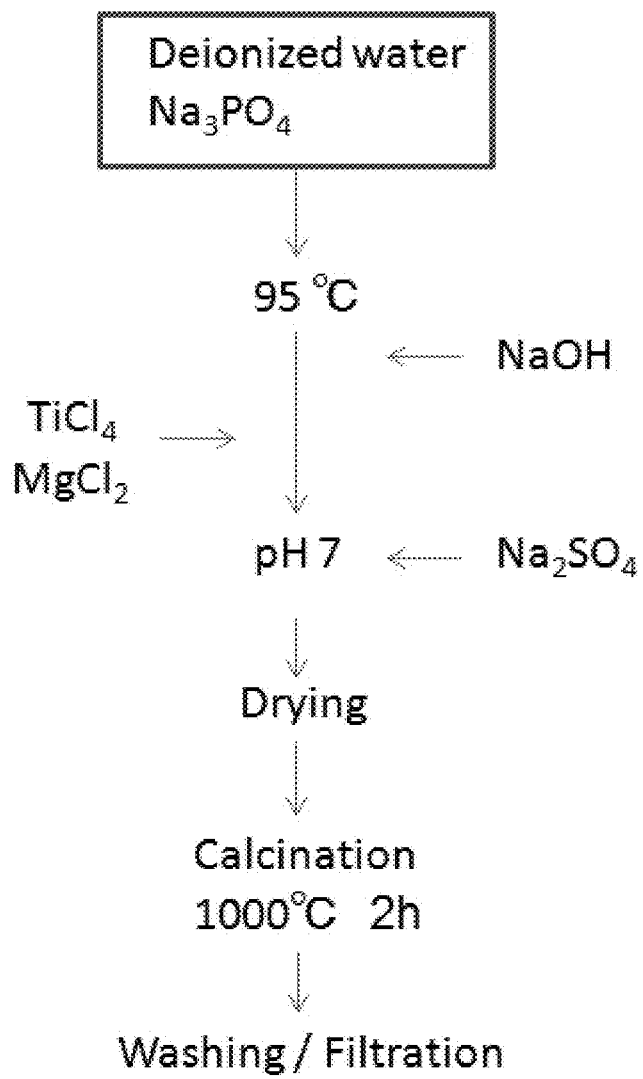
FIG. 2 is a flowchart showing the production method for the production of single crystalline $MgTiO_3$ flakes in accordance with a preferred embodiment of the present invention.

Hereinafter, the present invention will be described in more detail by referencing an example, however, the present invention is not limited to this example.

EXAMPLE 1

Into 1600 g of deionized water, 5.6 g of sodium phosphate is added and stirred while heating to 95° C. Into this solution, a total amount of 210 g of titanium tetrachloride solution (including 64 g of titanium tetra-chloride and 10 g of magnesium dichloride, 32.0% concentration in water) is added over the course of two hours while adjusting the pH with sodium hydroxide aqueous solution (32.0% concentration). After adding all of titanium tetrachloride solution, the pH is raised to 7. Further, 130 g of sodium sulfate is added under stirring. Afterwards, the resulting solution is dried and, finally, calcined at 1000° C. for two hours. After cooling, the obtained product is washed within warm water under agitation in order to remove chloride and sodium sulfate, and the $MgTiO_3$ flakes are obtained.

The obtained $MgTiO_3$ flakes have an average particle diameter of 30 μm and most of them show a circle shape or hexagonal shape. From the X-ray diffraction analysis, the main surface of the flake exhibits the (100) orientation and the crystal structure is the geikielite type. Further, the analysis with electron microscope confirmed that they are single crystals.

The single crystalline $MgTiO_3$ flakes obtained by the production method according to the present invention can be utilized as pigments for paints, inks, coating compositions, plastics, and cosmetics, and as photocatalysts, host material for dye sensitized solar cells, UV absorbents or as water repellents.

The invention claimed is:
1. A method for preparing single crystalline $MgTiO_3$ flakes by the following steps:
   a) forming a $MgTiO_3$ precursor by mixing at least a titanium compound, a magnesium compound and a phosphorous compound in an aqueous medium, which is held at a pH value of 6 to 8, and
   b) calcining the $MgTiO_3$ precursor at a temperature of 800° C. to 1400° C. as a single calcination step.

2. The method according to claim 1, wherein a fluxing agent is present in the mixing step.

3. The method according to claim 2, wherein the fluxing agent is one or more compounds selected from the group consisting of: $Na_2SO_4$, $K_2SO_4$, NaCl and KCl.

4. The method according to claim 1, which further comprises drying the $MgTiO_3$ precursor prior to the calcination step.

5. The method according to claim 1, wherein the calcining is in an oxygen containing atmosphere.

6. The method according to claim 2, wherein a product obtained in the calcination step is treated with water.

7. The method according to claim 1, wherein the titanium compound is one or more compounds selected from the group consisting of: titanium tetrachloride, titanyl sulfate, titanium sulfate and titanium trichloride.

8. The method according to claim 1, wherein the magnesium compound is one or more compounds selected from the group consisting of: magnesium chloride, magnesium sulfate and magnesium carbonate.

9. The method according to claim 1, wherein the phosphorous compound is one or more compounds selected from the group consisting of: trisodium phosphate, phosphorous pentoxide, phosphoric acid, phosphorous acid and tripotassium phosphate.

10. The method according to claim 1, wherein the single crystalline $MgTiO_3$ flakes prepared have a geikielite crystal structure.

11. The method according to claim 1, wherein the single crystalline $MgTiO_3$ flakes prepared have a particle diameter of 10 to 100 μm, according to an equivalent of a corresponding circle diameter.

12. The method of claim 1, wherein the aqueous medium is held at a pH value of 7.

13. The method of claim 1, wherein the phosphorus compound is a phosphate compound.

14. The method of claim 1, wherein the phosphorus compound is one or more compounds selected from the group consisting of phosphoric acid, phosphates, condensed phosphoric acid, and condensed phosphate.

15. The method of claim 1, wherein the calcining of the $MgTiO_3$ precursor is at a temperature of greater than 1000° C. to 1250° C. as a single calcination step.

16. A method for preparing single crystalline $MgTiO_3$ flakes by the following steps:
   a) forming a $MgTiO_3$ precursor by mixing at least a titanium compound, a magnesium compound and a phosphorous compound in an aqueous medium, and
   b) calcining the $MgTiO_3$ precursor at a temperature of 800° C. to 1400 ° C. as a single calcination step,
   wherein
      a fluxing agent is present in the mixing step, which is one or more compounds selected from the group consisting of: $Na_2SO_4$, $K_2SO_4$, NaCl and KCl,
   and/or
      the phosphorous compound is one or more compounds selected from the group consisting of: trisodium phosphate, phosphorous pentoxide, phosphorous acid and tripotassium phosphate.

17. A method for preparing single crystalline $MgTiO_3$ flakes by the following steps:
   a) adding a phosphorous compound, a titanium compound and a magnesium compound to an aqueous medium, forming a $MgTiO_3$ precursor by mixing at least the titanium compound, the magnesium compound and the phosphorous compound in the aqueous medium, wherein the phosphorous compound is added to the aqueous medium prior to the addition of the titanium compound and/or the magnesium compound to the aqueous medium, and
   b) calcining the $MgTiO_3$ precursor at a temperature of 800° C. to 1400° C. as a single calcination step.

18. The method of claim 17, wherein the phosphorous compound is added to the aqueous medium prior to the addition of the titanium compound to the aqueous medium.

19. The method of claim 17, wherein the phosphorous compound is added to the aqueous medium prior to the addition of the magnesium compound to the aqueous medium.

20. The method of claim 17, wherein the aqueous medium is held at a pH value of 6 to 8.

* * * * *